(12) United States Patent
Green

(10) Patent No.: US 8,110,397 B2
(45) Date of Patent: Feb. 7, 2012

(54) SAMPLE PREPARATION APPARATUS

(75) Inventor: Douglas Jason Green, Baltimore, MD (US)

(73) Assignee: Smiths Detection Inc., Edgewood, MD (US)

(*) Notice: Subject to any disclaimer, the term of this patent is extended or adjusted under 35 U.S.C. 154(b) by 0 days.

(21) Appl. No.: 12/172,144

(22) Filed: Jul. 11, 2008

(65) Prior Publication Data

US 2009/0075344 A1    Mar. 19, 2009

Related U.S. Application Data

(60) Provisional application No. 60/929,793, filed on Jul. 12, 2007.

(51) Int. Cl.
*C12M 1/26* (2006.01)
*C12M 3/00* (2006.01)

(52) U.S. Cl. ............ 435/309.1; 435/287.6; 435/287.7; 435/288.2; 435/288.7

(58) Field of Classification Search .............. 435/91.2, 435/309.1, 165, 287.6–288.7; 600/572, 569, 600/584, 575
See application file for complete search history.

(56) References Cited

U.S. PATENT DOCUMENTS

| | | | |
|---|---|---|---|
| 5,965,453 A | 10/1999 | Skiffington et al. | |
| 6,780,160 B2 * | 8/2004 | Zhou et al. | 600/562 |
| 7,238,520 B2 * | 7/2007 | Brown et al. | 435/287.6 |
| 7,993,871 B2 * | 8/2011 | Skiffington et al. | 435/30 |
| 2004/0161788 A1 * | 8/2004 | Chen et al. | 435/6 |
| 2004/0209266 A1 * | 10/2004 | Squirrell | 435/6 |
| 2004/0214200 A1 | 10/2004 | Brown et al. | |
| 2008/0206751 A1 * | 8/2008 | Squirrell et al. | 435/6 |

FOREIGN PATENT DOCUMENTS

| | | |
|---|---|---|
| EP | 1 661 988 A1 | 5/2006 |
| WO | WO 2005/049809 A1 | 6/2005 |
| WO | 2006079814 | 8/2006 |

OTHER PUBLICATIONS

International Search Report and Written Opinion dated Feb. 9, 2009, received in corresponding International Application No. PCT/US2008/008561 (15 pgs.).

* cited by examiner

*Primary Examiner* — Michael Marcheschi
*Assistant Examiner* — Shanta G Doe
(74) *Attorney, Agent, or Firm* — Casimir Jones, S.C.

(57) ABSTRACT

A reconfigurable sample preparation device includes a rotary plunger device having a hollow body and a coupling device, provided above one end of the rotary plunger, and accommodating a sample. The device also includes at least one sealed reagent module. When the rotary plunger is rotated on the coupling device, a film of the reagent module is pierced, mixing the sample with a substance from the reagent module.

14 Claims, 3 Drawing Sheets

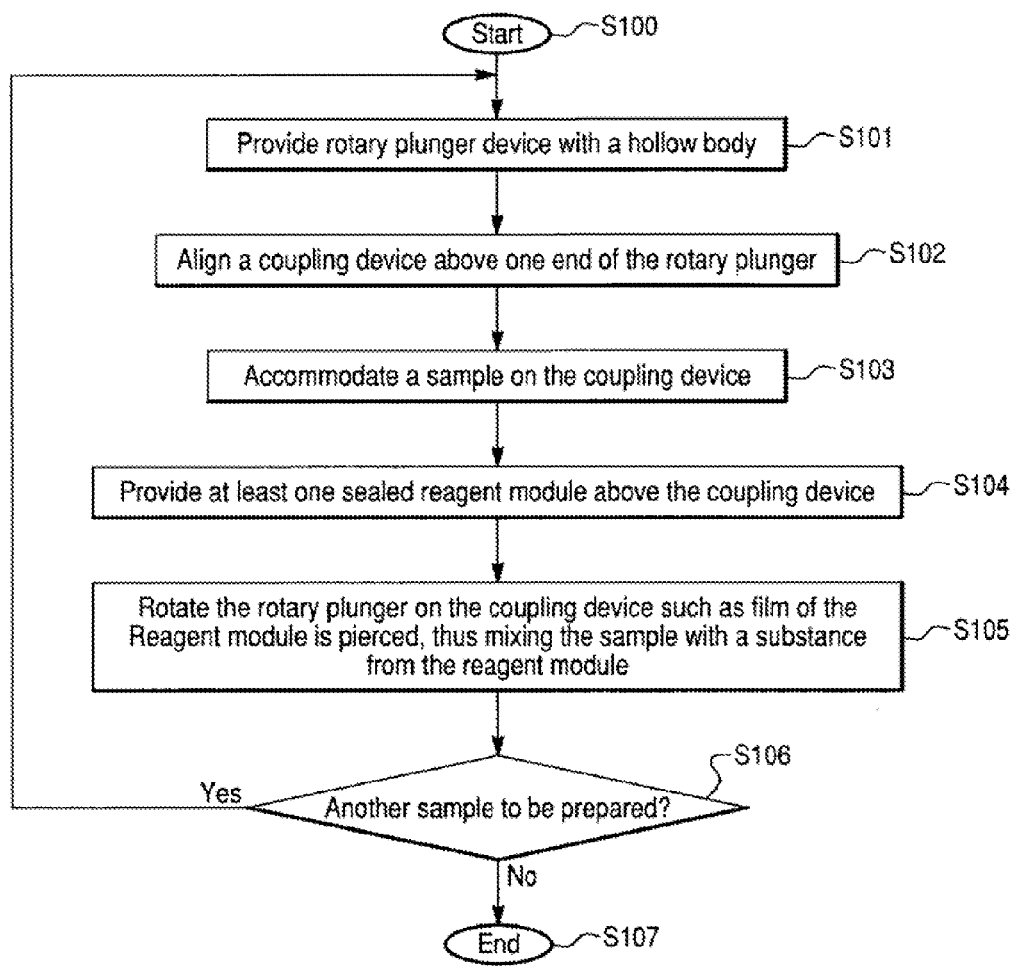

SAMPLE PREPARATION APPARATUS

BACKGROUND

Biological samples often must be prepared prior to analysis. For example, before a biological sample can be analyzed using a polymerase chain reaction (PCR) technique, the sample must be collected and processed to extract nucleic acids. Often, three steps generally must be performed. First, inhibitors such as humic acids and metals in the environment from which the sample is obtained are removed. Second, the sample is filtered and concentrated. Third, reagents for the PCR assay are added to the sample. Sample preparation may often include additional steps, such as sample cell lysis and washing of sample. These steps can be very time consuming and may require the skill of experienced laboratory personnel.

Because biological sample preparation often involves a number of complicated steps, field personnel often lack the equipment or skill necessary to prepare sample and perform analytical techniques. Thus, rather than being able to prepare and analyze samples in the field, a sample often must be transported to a laboratory facility for preparation and analysis. This can result in delay that can cause spread of pathological agents, added cost, sample loss, and contamination. These disadvantages are particularly problematic when dealing with pathogenic microorganism, including biowarfare agents. Thus, a need exists for a sample preparation device that easily can be used in the field by personnel with limited training.

Some consumable sample preparation devices are known. However, these sample preparation devices suffer from a number of disadvantages. For example, portable sample preparation devices generally cannot be easily reconfigured. They come pre-loaded with reagents that may not be appropriate for all applications, which results in the need for different sample preparation devices depending on the application.

In addition, consumable sample preparation devices often require multiple steps of sample manipulation prior to introduction into a analysis device. For example, sample may have to be manually moved from one reagent chamber to another. Such steps can be time consuming and can result in contamination or loss of sample.

Therefore, a need exists for a biological sample preparation device that can be easily reconfigured and allows simple preparation of a sample.

SUMMARY OF THE DISCLOSURE

Accordingly, a sample preparation device is disclosed that provides for ease of use and reconfiguration. One embodiment provides a sample preparation device that includes a rotary plunger device having a hollow body and a coupling device, provided above one end of the rotary plunger, and accommodating a sample. The device also includes at least one sealed reagent module. When the rotary plunger is rotated on the coupling device, a film of the reagent module is pierced, mixing the sample with a substance from the reagent module.

According to another embodiment, a method for creating a sample preparation device includes providing a rotary plunger device with a hollow body and aligning a coupling device above one end of the rotary plunger. The method also includes accommodating a sample on the coupling device, providing at least one sealed reagent module above the coupling device and rotating the rotary plunger on the coupling device such that a film of the reagent module is pierced, thus mixing the sample with a substance from the reagent module.

BRIEF DESCRIPTION OF THE DRAWINGS

FIG. 2 is a flowchart depicting steps performed within the reconfigurable sample preparation device in accordance with one embodiment.

DETAILED DESCRIPTION

A sample preparation device and methods for its use and construction are disclosed. In the following description, numerous details are set forth. It will be appreciated, however, to one skilled in the art, that embodiments may be practiced without these specific details. In other instances, well-known structures and devices are shown in block diagram form, rather than in detail.

Figure 1:
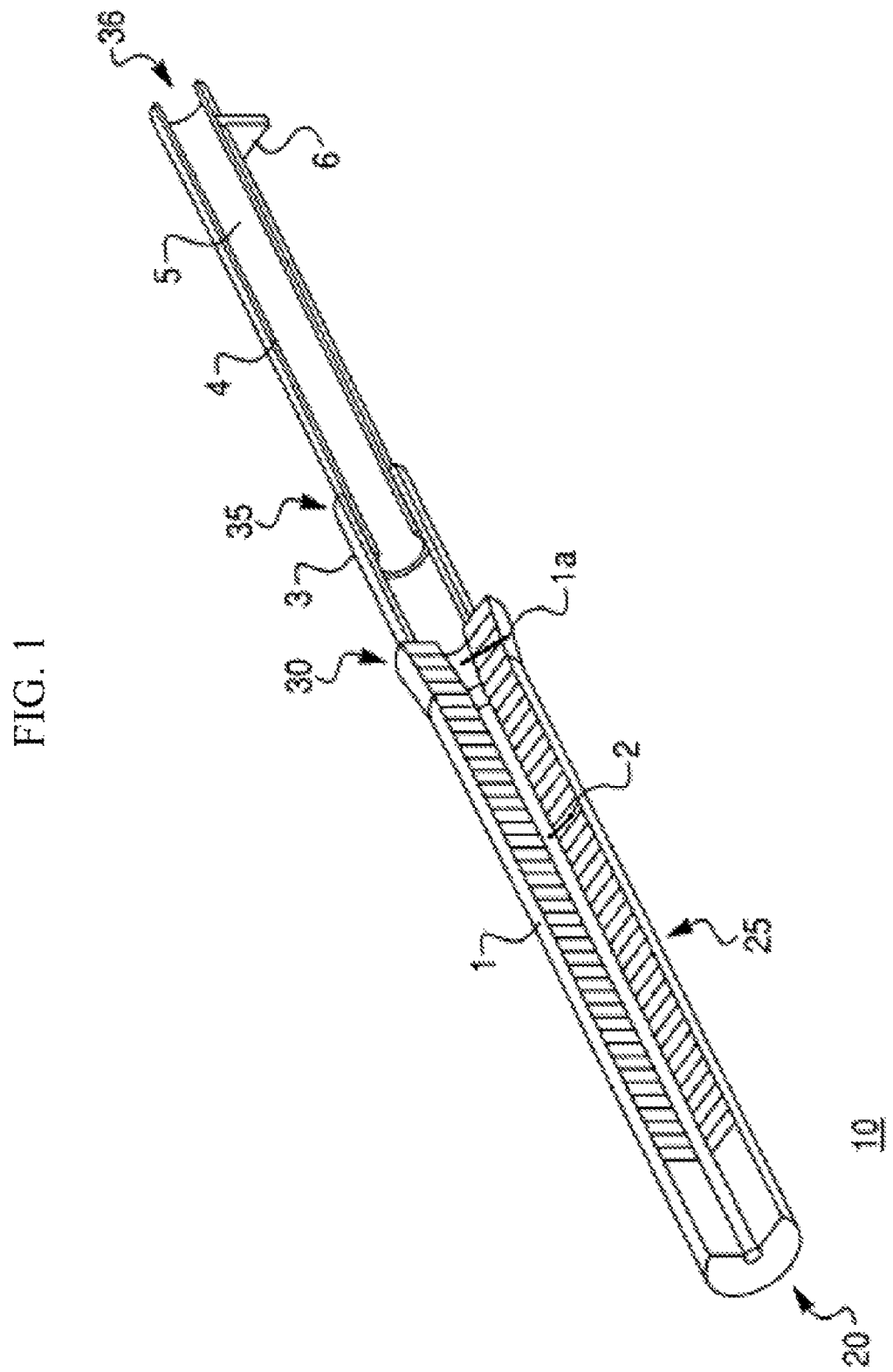
FIG. 1 illustrates a cross sectional view of a reconfigurable sample preparation device in accordance to one embodiment.

FIG. 1 illustrates a cross sectional view of a sample preparation device. The sample preparation device, generally noted by reference numeral 10, includes a rotary plunger device 1, a membrane piercing device 1a, a wand 2, a coupling device 3, and a reagent module 4.

According to one embodiment, the rotary plunger 1 has a proximal end 20, a distal end 30 and a hollow body 25. The membrane piercing device 1a can be provided at the distal end 30 of the rotary plunger 1. The membrane piercing device 1a can be made of any suitable material, such as a plastic or metal material. The material from which the membrane piercing device 1a can be made should preferably be compatible with the reagents and not interfere with the sample. A wand 2 can be accommodated in the hollow body 25, extending from the proximal end 20 to the distal end 30 of the rotary plunger 1. The wand 2 can be a magnetic wand. The hollow body 25 can be made to accommodate magnetic wands that are already commercially available.

Coupling device 3 has a proximal end 35 and a distal end 36. The proximal end of coupling device 3 can be adapted to be in mechanical communication with rotary plunger 1, as discussed in greater detail below. The coupling device 3 can be in mechanical communication with the rotary plunger 1 using any means, including threads corresponding to threads on the rotary plunger, a frictional connection, or some other type of mechanical communication. The distal end of the coupling device 3 can be adapted to hold one or more reagent modules 4, as discussed in greater detail below. The coupling device 3 can hold one or more reagent modules 4 using any suitable means, including threads corresponding to threads on the exterior of the reagent module 4, a frictional connection with the reagent module 4, or any other suitable means.

Figure 3A:
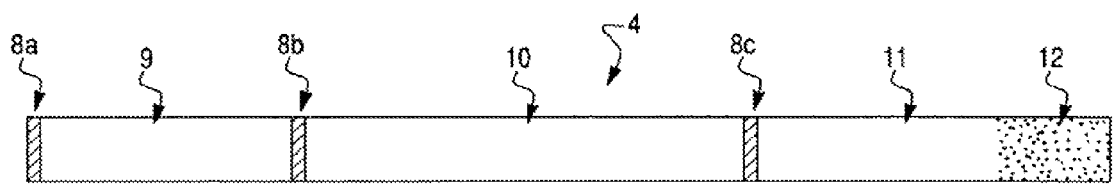
FIG. 3 illustrates some exemplary configurations of reagent module 4.

Sample can be introduced to the sample preparation apparatus in a number of different ways. Coupling device 3 can receive an initial sample at proximal end 35. The sample can be placed into the coupling device 3 by any means, such as a pipette or swab. The coupling device 3 may be adapted to receive the sample. For example, coupling device 3 may include a buffer solution or a sorbent material, such as cotton, to receive the sample. Sample can also be initially placed in hollow tube 25 either distally or proximally to membrane piercing device 1a. To accommodate the sample, hollow tube 25 may contain a sorbent material. As yet another alternative, sample can be initially received by a reagent module 4. For example, a reagent module 4 may have three chambers each separated by seals 8a, 8b, and 8c, as illustrated in FIG. 3a. Sample can be introduced into the first chamber 9 by piercing the first seal 8a. The second chamber 10 and third chamber 11 can contain a buffer and a sorbent material, respectively, for further preparation of the sample. These chambers can be accessed during operation of the device by the membrane piercing device 1a or wand 2 sequentially penetrating seal 8b and seal 8c.

The reagent module 4 can be in any configuration. For example, the reagent module 4 can contain one or more chambers sealed, such that the contents of each chamber do not come into contact with each other, unless the seals separating the chambers are pierced. The chambers can contain magnetic beads, buffer, reagent, or absorbent material. The seal can be made of any suitable material, such as foil or a plastic. The reagent module 4 can be constructed for a specific application. For example, reagent module 4 can contain all of the reagents for a specific type of analysis. In the alternative, different reagent modules 4 can be made for each reagent, such that different combination of reagent module 4 can be used depending on the specific type of sample preparation desired. Reagent module 4 can also be configured to allows a user to add the desired reagent or change the reagents. For example, reagent module 4 can include an injection port at the distal end to inject or remove content, such as magnetic beads, buffer, and reagent.

Figure 3B:
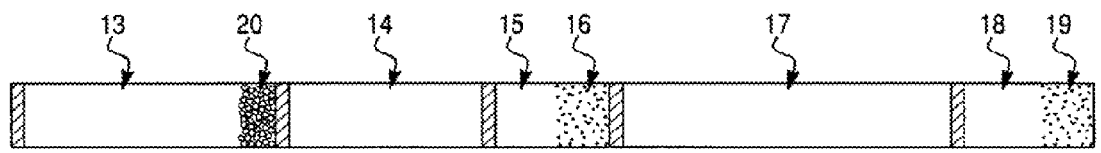

FIG. 3 illustrates some reagent module 4 configurations. FIG. 3a shows a reagent module 4 having a first chamber 9, a second chamber 10 and a third chamber 11 containing a sorbent material 12. These three chambers are separated by a seals 8a, 8b, and 8c. In one embodiment, first chamber 9 contains a buffer solution, second chamber 10 contains a reagent, and third chamber 11 contains a sorbent material to absorb the buffer and reagent. FIG. 3b shows a reagent module 4 having a first chamber 13, a second chamber 14, a third chamber 15, a fourth chamber 17, and a fifth chamber 18. The third chamber 15 and fifth chamber 19 have sorbent materials 16 and 19, respectively. The first chamber 13 can contain a buffer with magnetic beads 20, the second chamber 14 can contain a lysis solution, the third chamber 15 can absorb the buffer and lysis solution, the fourth chamber 17 can have a wash buffer to wash material bound to the magnetic beads, and the fifth chamber can contain sorbent material 19 to absorb wash buffer from the fourth chamber 17. Other configurations can be readily made based on the specific application.

Reagent module 4 can be attached to other reagent modules using a reagent module coupler 20. Reagent modular coupler 20 can allow a number of reagent modules to be connected serially. The reagent modular coupler 20 can couple two reagent modules using a frictional fitting, or it can contain threads corresponding to threads found on the exterior of the reagent modules. A reagent module coupler 20 does not need to be used in order to use more than one reagent module 4. Different reagent modules 4 can also be used by simply detaching one reagent module 4 from coupler 3 and attaching a different reagent module 4. The sample prepared using the first reagent module 4 can be transferred to the second reagent module 4 using magnetic beads and the wand 2.

Reagent module 4 can include a sample module 6. This sample module 6 can be used to hold the final prepared sample for analysis. For example, sample module 6 can be a cuvette. Sample module 6 can be an integral part of the reagent module 6 or it can be coupled to the reagent module 4.

In one embodiment of operation, rotary plunger device 1 can be placed in mechanical communication with coupling device 3 by twisting the rotary plunger 1 onto the coupling device 3. The membrane piercing device 1a pierces a seal 9 exposing sample 7 to the contents of reagent module 4. If the reagent module 4 contains more than one chamber, the sample can be exposed to each chamber sequentially by screwing reagent module 4 into the rotary plunger device 4. The sample 7 can also be exposed to each chamber sequentially by using the magnetic plunger 2 to pierce the seals separating chambers. In this manner, sample 7 can be sequentially exposed to the contents of one or more reagent modules 4 each containing one or more chambers.

According to one embodiment, the magnetic wand 2 can be inserted or retracted within the hollow body 25 to attract or release a magnetic beads. The sample can be pre-mixed with magnetic beads before loading or the magnetic beads can be contained in a chamber of reagent module 4. The magnetic bead mix can be utilized for the isolation and separation of particles in the sample. For example, the analyte can be bound to the magnetic beads and by advancing the magnetic beads through each chamber using the magnetic wand 2, the analyte can be exposed to the contends of each chamber sequentially. In one embodiment, the magnetic beads may be designed to bind nucleic acid.

According to the operation, since the rotary plunger 1 can be only coupled to the coupling device 3, it can be easily detached from the coupling device 3 for another sample to be received by the coupling device 3. Thus, many samples can be prepared in an expeditious manner. The motion of the rotary plunger 1, and specifically the embedded magnetic wand 2, may be controlled by a user, or may be attached to another apparatus such that it is an automated process. Similarly, the magnetic wand may be inserted or retracted into the sample module 6, in either a user-regulated or automated fashion. The repeated insertion or retraction of the magnetic wand may allow for maximum contact of the magnetic beads with the contents of the reagent module 4.

The sample preparation device can be made a consumable. In other words, the sample preparation device can be disposed of after a single use. In the alternative, only portions of the sample preparation device may be consumable. For example, the rotary plunger device 1 can be made for repeated uses, and the coupling device 3 and reagent module 4 can be discarded after each use. The reusable components can be made of a material that does not degrade or become damaged after repeated decontamination treatments.

According to one embodiment, the reconfigurable sample preparation device can be used for DNA purification. DNA purification is a process by which DNA is extracted from cells and separated from other nuclear and cellular material. DNA is often extracted from various different types of samples. Thus, the ability to have a reconfigurable device with different numbers of reagent fluids or sorbents is ideal, because different reactions and different steps are necessary to extract DNA from different types of samples. Examples of samples from which DNA could be extracted include, but are not limited to, bacteria, viruses, plants, and animals, to name a few. Depending on the source of the sample, different reagents and sample preparation steps must be used. Thus, the easy manner in which reagent module 4 can be configured makes them well-suited for use in DNA purification.

According one embodiment, once the sample preparation is finished, the sample is analyzed using polymerase chain reaction (PCR). In a further embodiment, the reconfigurable sample preparation device can be utilized for PCR in a portable environment. The ability to use different sample modules 6 based upon the sample obtained, while using the same rotary plunging device 1, is ideal for portable situations, to maintain efficiency and ease of use. A sample holder 6 may be then inserted and utilized in a fluorimeter, or some other apparatus to carry out the PCR reaction.

The sample preparation device can be used in the field to prepare sample, but the sample preparation device can also be utilized in laboratory settings. Magnetic bead separation technology is known to be utilized and effective with fresh, frozen, and archival samples. DNA purification through this method and utilizing this device is advantageous, because it does not offer a large amount of mechanical stress, nor does it expose the sample to chemical or physical treatment. In addition, the method is easily controlled and repeatable. Further, the reconfigurable sample preparation device is scalable, and does not involve laborious or time-consuming processes to obtain an end result.

FIG. 2 is a flowchart depicting steps performed within the reconfigurable sample preparation device in accordance with one embodiment. The process begins from a start state S100 and proceeds to process step S101, where a rotary plunger device with a hollow body is provided. At process step S102, a coupling device is aligned above one end of the rotary plunger. At process step S1103, a sample can be accommodated on the coupling device. After the sample has been accommodated, at process step S104, at least one sealed reagent module can be provided above the coupling device. After the sealed reagent module has been provided, at process step S105, the rotary plunger can be rotated on the coupling device such that a film of the reagent module is pierced, thus mixing the sample with a substance from the reagent module. After the sample has been prepared, the process proceeds to decision step S106 where it is determined whether another sample is to be prepared. If another sample is to be prepared, the process returns to process step S101, otherwise, the process terminates at state S107.

Based on this description of exemplary embodiments, other embodiments will be readily apparent to one of skill in the art. Thus, these exemplary embodiments should be considered as limiting the scope, which is defined according to the following claims.

What is claimed is:

1. A sample preparation device, comprising:
    a rotary plunger device having a distal end, a proximal end and a hollow body, wherein the hollow body is accessible from the proximal end;
    a magnetic wand received in the hollow body of the rotary plunger device;
    a coupling device having a first end, a second end, and an inside cavity, wherein the first end of the coupling device is attached to the distal end of the rotary plunger; and
    at least one sealed reagent module comprising at least one chamber and at least one seal, wherein the at least one reagent module is attached to the second end of the coupling device,
    wherein rotation of the rotary plunger on the coupling device pierces the seal of the reagent module.

2. The sample preparation device according to claim 1, wherein the reagent module chamber contains a reagent fluid.

3. The sample preparation device according to claim 1, wherein the rotating plunger pierces the reagent module in a linear manner.

4. The sample preparation device according to claim 1, further comprising a membrane piercing device provided on the rotary plunger device.

5. The sample preparation device according to claim 1, wherein the magnetic wand is inserted or retracted to attract or release a magnetic bead mix.

6. The sample preparation device according to claim 4, wherein the membrane piercing device is made of plastic.

7. The sample preparation device according to claim 1, wherein the inside cavity of the coupling device comprises a sorbent material.

8. A method for operating a sample preparation device, comprising:
    providing a rotary plunger device having a distal end, a proximal end and a hollow body, wherein the hollow body is accessible from the proximal end, and wherein a magnetic wand is received in the hollow body;
    aligning a coupling device above one end of the rotary plunger, wherein the coupling device has a first end, a second end, and an inside cavity;
    accommodating a sample on the coupling device;
    providing at least one sealed reagent module above the coupling device; and
    rotating the rotary plunger on the coupling device such that a film of the reagent module is pierced, thus mixing the sample with a substance from the reagent module.

9. The sample preparation device according to claim 1, wherein the coupling device has threads at its second end, and wherein the at least one sealed reagent module has threads on its exterior corresponding to the threads at the second end of the coupling device.

10. The sample preparation device according to claim 1, wherein the at least one sealed reagent module comprising a plurality of chambers separated by seals.

11. The sample preparation device according to claim 10, wherein at least one of the chambers contains magnetic beads.

12. The method for operating a sample preparation device of claim 8, further comprising:
    providing magnetic beads premixed with the sample; and
    retracting the magnetic wand;
    wherein the analyte module comprises multiple chambers, and retracting the magnetic wand causes analyte bound to the magnetic beads to be exposed to contents of each chamber.

13. A sample preparation device, comprising:
    a rotary plunger device having a first end, and a second end and having a hollow body, wherein the hollow body is accessible from either the first end or the second end;
    a coupling device having a first end, a second end, and an inside cavity, wherein the first end of the coupling device is attached to the first end of the rotary plunger;
    at least one sealed reagent module comprising at least one chamber and at least one seal, wherein the at least one reagent module is attached to the second end of the coupling device, and
    a magnetic wand received in the hollow body of the rotary plunger device,
    wherein rotation of the rotary plunger on the coupling device pierces the seal of the reagent module.

14. The sample preparation device according to claim 1, wherein the at least one reagent module is closer to said distal end, than said proximal end, of said rotary plunger and attached to the second end of the coupling device.

* * * * *